United States Patent
Ribble et al.

(10) Patent No.: US 9,642,967 B2
(45) Date of Patent: May 9, 2017

(54) CATHETER MONITOR INTEGRATION WITH PATIENT SUPPORT, HYGIENE AND HEALTHCARE COMMUNICATION SYSTEMS

(71) Applicant: Hill-Rom Services, Inc., Batesville, IN (US)

(72) Inventors: David L. Ribble, Indianapolis, IN (US); Nicholas A. Mann, Cincinnati, OH (US); Brian L. Lawrence, Cincinnati, OH (US); Kirsten M. Emmons, Batesville, IN (US); Eric D. Agdeppa, Cincinnati, OH (US); Michael S. Hood, Batesville, IN (US); Robert M. Zerhusen, Cincinnati, OH (US); Joshua P. Lingenfelser, Fuquay Varina, NC (US); Steven A. Dixon, Riverview, FL (US); Ryan S. Severns, Grand Rapids, MI (US)

(73) Assignee: Hill-Rom Services, Inc., Batesville, IN (US)

( * ) Notice: Subject to any disclaimer, the term of this patent is extended or adjusted under 35 U.S.C. 154(b) by 7 days.

(21) Appl. No.: 14/829,692

(22) Filed: Aug. 19, 2015

(65) Prior Publication Data

US 2016/0136356 A1    May 19, 2016

Related U.S. Application Data

(60) Provisional application No. 62/081,277, filed on Nov. 18, 2014.

(51) Int. Cl.
| | | |
|---|---|---|
| *H01C 3/10* | (2006.01) | |
| *A61M 5/172* | (2006.01) | |
| (Continued) | | |

(52) U.S. Cl.
CPC ............ *A61M 5/172* (2013.01); *A61B 5/002* (2013.01); *A61B 5/208* (2013.01); *A61G 7/018* (2013.01);
(Continued)

(58) Field of Classification Search
CPC ..... G01F 23/0061; G01F 3/00; A61B 10/007; G05D 7/0676
(Continued)

(56) References Cited

U.S. PATENT DOCUMENTS

| | | |
|---|---|---|
| 5,561,412 A | 10/1996 | Novak et al. |
| 5,699,038 A | 12/1997 | Ulrich et al. |
| (Continued) | | |

FOREIGN PATENT DOCUMENTS

| | | |
|---|---|---|
| GB | 2492028 A | 12/2012 |
| WO | WO2009/055635 A1 | 4/2009 |
| (Continued) | | |

OTHER PUBLICATIONS

Hill-Rom Progressa™ Bed Service Manual, 2013 (293 pages).
(Continued)

*Primary Examiner* — Toan N Pham
(74) *Attorney, Agent, or Firm* — Barnes & Thornburg LLP

(57) ABSTRACT

Catheter monitor integration with patient support systems, such as patient beds, and with other healthcare communication systems including hand hygiene systems is provided. A patient bed that transmits bed data and catheter monitor data is disclosed. When catheter tubing is connected to a catheter monitor integrated into a patient bed, the bed automatically implements a falls prevention protocol. A countdown timer pertaining to removal of catheter tubing from a patient is displayed on one or more display devices. Monitoring for caregiver handwashing compliance in con-
(Continued)

nection with use of a catheter monitor or a catheter kit is also provided.

30 Claims, 4 Drawing Sheets

(51) Int. Cl.

| | | |
|---|---|---|
| A61H 9/00 | (2006.01) | |
| A61B 5/20 | (2006.01) | |
| A61G 7/018 | (2006.01) | |
| A61M 25/00 | (2006.01) | |
| A61M 5/50 | (2006.01) | |
| A61G 7/05 | (2006.01) | |
| A61G 7/08 | (2006.01) | |
| G06F 19/00 | (2011.01) | |
| A61B 5/00 | (2006.01) | |

(52) U.S. Cl.
CPC ......... *A61G 7/0507* (2013.01); *A61G 7/0524* (2016.11); *A61G 7/0528* (2016.11); *A61G 7/08* (2013.01); *A61H 9/0092* (2013.01); *A61M 5/5086* (2013.01); *A61M 25/0017* (2013.01); *G06F 19/327* (2013.01); *G06F 19/3406* (2013.01); *G06F 19/3418* (2013.01); *A61B 5/6852* (2013.01); *A61B 2562/227* (2013.01); *A61M 2205/18* (2013.01); *A61M 2205/3561* (2013.01); *A61M 2205/505* (2013.01); *A61M 2205/60* (2013.01)

(58) Field of Classification Search
USPC .... 340/286.07, 573.1; 5/658, 600, 618, 620; 52/36.4
See application file for complete search history.

(56) References Cited

U.S. PATENT DOCUMENTS

| | | | |
|---|---|---|---|
| 5,838,223 | A | 11/1998 | Gallant et al. |
| 6,208,250 | B1 | 3/2001 | Dixon et al. |
| 6,438,776 | B2 | 8/2002 | Ferrand et al. |
| 6,462,656 | B2 | 10/2002 | Ulrich et al. |
| 6,539,393 | B1 | 3/2003 | Kabala |
| 6,727,818 | B1 | 4/2004 | Wildman et al. |
| 6,924,441 | B1 | 8/2005 | Mobley et al. |
| 6,972,683 | B2 | 12/2005 | Lestienne et al. |
| 7,092,376 | B2 | 8/2006 | Schuman |
| 7,242,306 | B2 | 7/2007 | Wildman et al. |
| 7,248,933 | B2 | 7/2007 | Wildman |
| 7,253,366 | B2 | 8/2007 | Bhai |
| 7,319,386 | B2 | 1/2008 | Collins, Jr. et al. |
| 7,399,205 | B2 | 7/2008 | McNeely et al. |
| 7,734,476 | B2 | 6/2010 | Wildman et al. |
| 7,763,877 | B2 | 7/2010 | Paz |
| 7,852,208 | B2 | 12/2010 | Collins, Jr. et al. |
| 7,907,053 | B2 | 3/2011 | Wildman et al. |
| 8,046,625 | B2 | 10/2011 | Ferguson et al. |
| 8,169,304 | B2 | 5/2012 | Schuman, Sr. et al. |
| 8,384,526 | B2 | 2/2013 | Schuman, Sr. et al. |
| 8,471,231 | B2 | 6/2013 | Paz |
| 8,568,387 | B2 | 10/2013 | Paz |
| 8,598,995 | B2 | 12/2013 | Schuman et al. |
| 8,827,924 | B2 | 9/2014 | Paz et al. |
| 9,144,449 | B2 * | 9/2015 | Burr .................. A61B 18/0218 |
| 9,227,024 | B2 * | 1/2016 | Deutsch ............. A61M 5/5086 |
| 9,348,975 | B2 * | 5/2016 | Lo ........................... A61M 1/28 |
| 2003/0009952 | A1 * | 1/2003 | Gallant .................... A61G 7/00 52/36.4 |
| 2006/0100743 | A1 | 5/2006 | Townsend et al. |
| 2010/0286559 | A1 | 11/2010 | Paz et al. |
| 2012/0078137 | A1 * | 3/2012 | Mendels ................ A61B 5/205 600/584 |
| 2012/0089419 | A1 | 4/2012 | Huster et al. |
| 2012/0310670 | A1 | 12/2012 | Pruitt |
| 2014/0244298 | A1 | 8/2014 | Robinson et al. |
| 2014/0297327 | A1 | 10/2014 | Heil et al. |
| 2015/0081335 | A1 | 3/2015 | Dixon et al. |
| 2015/0173937 | A1 | 6/2015 | Jackson |
| 2015/0362351 | A1 * | 12/2015 | Joshi .................. G01F 23/0061 700/282 |

FOREIGN PATENT DOCUMENTS

| | | |
|---|---|---|
| WO | WO2009/135081 A1 | 11/2009 |
| WO | WO2014/150970 A1 | 9/2014 |

OTHER PUBLICATIONS

BARD Urological Catheter Systems brochure, 2005 (2 pages).
Healthcare Infection Control Practices Advisory Committee, *Guideline for Prevention of Catheter—Associated Urinary Tract Infections 2009* (67 pages).
Preventing Central Line-Associated Bloodstream Infections, A Global Challenge, A Global Perspective, The Joint Commission, 2012 (152 pages).
U.S. Appl. No. 62/073,098, filed Oct. 31, 2014 (41 pages).
U.S. Appl. No. 14/879,179, filed Oct. 9, 2015 (33 pages).
EP Search Report for Application No./Patent No. 15186016.0-1951, dated Apr. 18, 2016 (10 pages).
FlowSense Medical Ltd., Updated Company Presentation, May 2012, URL:trade.bankleumi.co.il/TRADE/info/shuk/shukgetfile. asp?fileid . . . (22 pages).

* cited by examiner

CATHETER MONITOR INTEGRATION WITH PATIENT SUPPORT, HYGIENE AND HEALTHCARE COMMUNICATION SYSTEMS The present application claims the benefit, under 35 U.S.C. §119(e), of U.S. Provisional Application No. 62/081,277, which was filed Nov. 18, 2014, and which is hereby incorporated by reference herein in its entirety.

BACKGROUND

The present disclosure relates to patient support systems such as patient beds and integration of other equipment with such patient support systems as well as with other healthcare communication systems and hand hygiene systems. More particularly, the present disclosure relates to integration of a catheter monitor into such systems.

Patient support systems, such as patient beds, used in healthcare facilities such as hospitals, long term care facilities, nursing homes, and the like, oftentimes support patients that are catheterized. Some such patient beds even have attachment points for urine collection receptacles such as Foley bags. In more recent times, catheter monitors have been developed to gather and monitor data regarding urine flow, volume, temperature, and the like. The catheter monitors are oftentimes used with kits that include catheter tubing and other disposables.

Patient beds that connect to a network of a healthcare facility to transmit bed data, bed alarms, and patient nurse calls to the network are known. For example, patient beds that send data to a nurse call system of a healthcare facility are known. Nurse call systems sometimes have nurse call system servers that are networked to other servers, such as an admission, discharge, and transfer (ADT) server or an electronic medical records (EMR) server, of a healthcare facility. Thus, bed data is able to be shared with other servers or systems in a healthcare facility. When patients are catheterized, it is desirable that they remain in bed. Thus, it is preferable that bed exit systems of patient beds are enabled when patients are catheterized. Currently, caregivers need to remember to manually enable a bed exit system on a patient bed when a patient is catheterized.

Based on the foregoing, caregivers may appreciate integration of a catheter monitor with a patient bed so that improved connectivity of the catheter monitor data to other healthcare information system results and so that improved alarming, caregiver monitoring of catheter monitor data, and improved compliance with healthcare protocols also results. Bed operations and protocols may also benefit from use of data from an integrated catheter monitor.

SUMMARY

The present application discloses one or more of the features recited in the appended claims and/or the following features which, alone or in any combination, may comprise patentable subject matter:

According to one aspect of the present disclosure, a patient bed may include a frame that may be configured to support a patient. A barrier may be coupled to the frame and may be configured to inhibit patient egress from the frame. A catheter monitor may be provided and the barrier may have a cavity that may be shaped to receive at least a portion of the catheter monitor.

The patient bed may further include bed control circuitry that may be carried by the frame and that may be configured to control at least one function of the patient bed. The catheter monitor may have monitor circuitry that may be in communication with the bed control circuitry. In some embodiments, the patient bed may have at least one graphical user interface (GUI) that may be coupled to the bed control circuitry. The GUI may be operable to display bed information that may pertain to the at least one function of the patient bed and to display monitor information that may pertain to at least one function of the catheter monitor.

In some embodiments, the bed control circuitry may be configured to communicate to a network of a healthcare facility bed information that may pertain to the at least one function of the patient bed and monitor information that may pertain to at least one function of the catheter monitor. Alternatively or additionally, the bed control circuitry may be configured to communicate to a network of a healthcare facility bed identification (ID) data and catheter monitor identification (ID) data. Further alternatively or additionally, the bed control circuitry may be configured to communicate to the network of the healthcare facility patient identification (ID) data.

The patient bed may further include an additional piece of patient care equipment and the cavity may be sized to receive at least a portion of the additional piece of patient care equipment when the catheter monitor is removed from the cavity. The additional piece of patient care equipment may comprise a pulse oximeter or a sequential compression device, for example.

According to another aspect of the present disclosure, a patient support apparatus may include a patient support structure to support a patient and control circuitry to control at least one function of the patient support structure. The control circuitry may be operable to implement a falls prevention protocol. A catheter monitor may be coupled to the patient support structure. The control circuitry may implement the falls prevention protocol in response to a signal from the catheter monitor indicating at least one of the following: the catheter monitor being turned on, a catheter tube being attached to the catheter monitor, and urine flowing through the catheter monitor.

In some embodiments, the falls prevention protocol may include an alert being generated to indicate that casters of the patient support apparatus are not braked. Alternatively or additionally, the falls prevention protocol may include an alert being generated to indicate that at least one siderail of the patient support apparatus is not in a raised position. Further alternatively or additionally, the falls prevention protocol may include an alert being generated to indicate that an upper frame of the patient support apparatus is not in a lowered position relative to a base frame of the patient support apparatus. Still further alternatively or additionally, the falls prevention protocol may include an alert being generated if a patient position monitoring system of the patient support apparatus indicates that the patient has exited the patient support apparatus or has moved toward exiting the patient support apparatus by a threshold amount.

It is contemplated by this disclosure that the control circuitry may send a nurse call signal to at least one remote nurse call system computer device in response to a violation of the falls risk protocol. In some embodiments, the control circuitry may send data to at least one remote computer device of an electronic medical records system and the data may pertain to operation of the catheter monitor or implementation of the falls risk protocol or both. Alternatively or additionally, the control circuitry may send data to at least one computer device that may signal an electronic room sign to display information that may pertain to the falls risk protocol.

According to a further aspect of the present disclosure, a patient support apparatus may include a patient support structure to support a patient and control circuitry to control at least one function of the patient support structure. A catheter monitor may be coupled to the patient support structure and may have monitor circuitry. At least one of the control circuitry and the monitor circuitry may be operable to implement a countdown timer. The countdown timer may be activated in response to a signal from the catheter monitor indicating at least one of the following: the catheter monitor being turned on, a catheter tube being attached to the catheter monitor, and urine flowing through the catheter monitor.

Expiration of the countdown timer may indicate, for example, a time at which the catheter is to be removed from the patient. In some embodiments, an initial period of time at which the countdown timer is set may be no longer than 24 hours. It is contemplated by this disclosure that an alert may be initiated by at least one of the control circuitry and the monitor circuitry in response to expiration of the countdown timer. Alternatively or additionally, an alert may be initiated by at least one of the control circuitry and the monitor circuitry a preset amount of time prior to the expiration of the countdown timer.

In some embodiments, the patient support apparatus may further include a graphical user interface (GUI) carried by the patient support structure and that may be coupled to at least one of the control circuitry and the monitor circuitry. The countdown timer may be displayed on the GUI.

In some embodiments, at least one of the control circuitry and the monitor circuitry may send a nurse call signal to at least one remote nurse call system computer device in response to expiration of the countdown timer or upon a preset amount of time prior to the expiration of the countdown timer being reached. Alternatively or additionally, at least one of the control circuitry and the monitor circuitry may send data to at least one remote computer device of an electronic medical records system that may pertain to the countdown timer. Further alternatively or additionally, at least one of the control circuitry and the monitor circuitry may send data to at least one computer device that may signal an electronic room sign to display information pertaining to the countdown timer. For example, the information pertaining to the countdown timer may include an amount of time left before expiration of the countdown timer may be reached.

According to still another aspect of the present disclosure, a system may include a patient bed that may have bed circuitry configured to sense bed data. A catheter monitor may be mounted to the patient bed and may have monitor circuitry to sense monitor data. At least one of the monitor circuitry and the bed circuitry may be in communication with the other. At least one remote computer device may receive the bed data and the monitor data that may be transmitted over a common communication link from the patient bed.

In some embodiments, the monitor data may include one or more of the following: tube connection data, temperature data, urine volume data, urine flow data, urinalysis data, catheter monitor identification (ID) data, catheter monitor diagnostic data, and catheter monitor alarm data. The monitor data may further include countdown to removal data. The monitor circuitry may include at least one optical sensor to sense the monitor data.

In some embodiments, the bed data may include one or more of the following: siderail position data, bed height data, mattress inflation data, bed identification (ID) data, bed alarm data, caster braking data, and bed diagnostic data. The common communication link may comprise a wired communication link or a wireless communication link, for example.

It is contemplated by this disclosure that the catheter monitor may include a housing, a module that may carry the monitor circuitry, and tubing that may couple to the module. The module may detachably couple to the housing such that the module with the monitor circuitry and the tubing may be disposable after use. The system may further include a collection receptacle that may couple to the tubing. The collection receptacle also may be disposable after use. The catheter monitor may include interface circuitry that may be carried by the housing. The interface circuitry may couple the monitor circuitry with the bed circuitry when the module is coupled to the housing.

In some embodiments, the patient bed includes a graphical user interface (GUI) that may be coupled to the bed circuitry and coupled to the monitor circuitry. The GUI may be operable to display the bed data and the monitor data. The patient bed may include a user input either on the GUI or separate from the GUI that may be selected by a caregiver to confirm the accuracy of at least some of the monitor data.

In some embodiments, the remote computer device also may receive patient data transmitted over the common communication link from the patient bed. The patient data may include one or more of the following: patient location data, patient identification (ID) data, patient vital signs data, patient weight data, and patient alarm data.

According to yet another aspect of the present disclosure, a system may include a patient bed and a catheter monitor that may be mounted to the patient bed. The catheter monitor may have a sensor that may sense connection of catheter tubing thereto. The system may also include a hand hygiene system that a caregiver may use for handwashing and that may monitor for handwashing compliance by caregivers. The system may further include a compliance monitoring computer that may, in response to catheter tubing being connected to the catheter monitor, determine whether the caregiver attaching the catheter tubing to the catheter monitor used the hand hygiene system for handwashing less than a threshold amount of time prior to connecting the catheter tubing to the catheter monitor.

In some embodiments, the system may further include a locating system that may determine the location of the caregiver in a healthcare facility. The locating system may be in communication with the hand hygiene system and with the compliance monitoring computer. It is contemplated by this disclosure that the threshold amount of time may be selectable using the compliance monitoring computer. An alert may be generated by the compliance monitoring computer if the catheter tubing is connected to the catheter monitor and the caregiver did not use the hand hygiene system within the threshold amount of time prior to connecting the catheter tubing to the catheter monitor. The alert may include a message displayed on at least one of the following: a graphical user interface (GUI) of the patient bed, a GUI of the catheter monitor, a room station of a nurse call system, an electronic room sign, a phone display, and a tablet computer display.

According to still a further aspect of the present disclosure, a system may include a catheter kit that may, in turn, include catheter tubing. The catheter kit may have a transmitter that may transmit a kit-opened signal indicating that the kit is being opened or has been opened. The system may include a hand hygiene system that a caregiver may use for handwashing and that may monitor for handwashing compliance by caregivers. The system may also include a compliance monitoring computer that may receive the kit-opened signal and that may determine whether the caregiver opening the catheter kit has used the hand hygiene system for handwashing within a threshold amount of time prior to or after receipt of the kit-opened signal.

In some embodiments, the system further includes a display that may display activities required by a healthcare protocol. The healthcare protocol may comprise, for example, activities that include one or more of: wearing a gown, wearing sterile gloves, wearing a mask, draping a patient with a sterile sheet, and use of an antiseptic such as chlorhexidine. The display may be included as part of one or more of the following: a nurse call computer, a room station of nurse call system, a GUI of a patient bed, an electronic room sign, a phone display, and a tablet computer display.

It is contemplated by this disclosure that the system may further include RF transmitters that may be affixed to one or more of the gown, the gloves, the mask, and the drape and may further include RF receivers that may receive signals from the RF transmitters to determine compliance with the healthcare protocol. The system may further include a locating system that may determine caregiver location. The locating system may be in communication with the hand hygiene system and with the compliance monitoring computer.

The compliance monitoring computer may receive caregiver identification (ID) data from the locating system and may determine whether the caregiver identified by the caregiver ID data has received proper training to implement the healthcare protocol. In some embodiments, the compliance monitoring computer may determine that a patient's condition meets established criteria for the healthcare protocol based on patient data received by the compliance monitoring computer.

Alternatively or additionally, the compliance monitoring computer may receive caregiver identification (ID) data and caregiver location data from the locating system and may confirm that the caregiver has not been exposed to infectious agents within a threshold amount of time prior to opening the catheter monitoring kit. An alert may be generated by the compliance monitoring computer if the caregiver has been exposed to infectious agents within the threshold amount of time. The alert may include a message displayed on at least one of the following: a graphical user interface (GUI) of a patient bed, a GUI of a catheter monitor, a room station of a nurse call system, an electronic room sign, a phone display, and a tablet computer display.

According to another aspect of the present disclosure, a system may include a patient bed that may have an RFID reader, a catheter tube, an RFID tag that may be attached to the catheter tube, and a timer that may begin a timing cycle in response to the RFID reader reading the RFID tag that may be attached to the catheter tube.

In some embodiments, the system may include metallic foil packaging in which the catheter tube and the RFID tag may be contained prior to use. The metallic foil packaging may prevent the RFID reader from reading the RFID tag until after the catheter tube with the RFID tag attached thereto are removed from the metallic foil packaging.

In some embodiments, the timing cycle may comprise a countdown time and expiration of the countdown time may indicate a time at which the catheter tube is to be removed from the patient. It is contemplated that, in some embodiments, an initial period of time at which the countdown time is set may be no longer than 24 hours. An alert may be initiated in response to expiration of the countdown time. Alternatively or additionally, an alert may be initiated a preset amount of time prior to the expiration of the countdown time.

In some embodiments, the patient bed may include a graphical user interface (GUI) carried and the countdown time may be displayed on the GUI. A nurse call signal may be sent to at least one remote nurse call system computer device in response to expiration of the countdown time or upon a preset amount of time prior to the expiration of the countdown time being reached. In some embodiments, the patient bed may send data to at least one remote computer device of an electronic medical records system pertaining to the countdown time. Alternatively or additionally, the patient bed may send data to at least one computer device that may signal an electronic room sign to display information pertaining to the countdown time. For example, the information pertaining to the countdown time may include an amount of time left before expiration of the countdown time is reached.

According to still another aspect of the present disclosure, a system may include a patient bed that may have an RFID reader, a catheter tube, an RFID tag that may be attached to the catheter tube, and a graphical user interface (GUI). In response to the RFID reader reading the RFID tag attached to the catheter tube, a prompt may be displayed on the GUI for an electronic input to be entered by a caregiver. The system may have a timer that may begin a timing cycle in response to entry of the electronic input by the caregiver on the GUI.

In some embodiments, the system may further include metallic foil packaging in which the catheter and the RFID tag may be contained prior to use. The metallic foil packaging may prevent the RFID reader from reading the RFID tag until after the catheter tubing with the RFID tag attached thereto are removed from the metallic foil packaging.

According to this disclosure, the GUI may be integrated into the patient bed or may be included as part of a room station of a nurse call system or may be included as part of a handheld controller such as handheld pendant controller of the patient bed. In some embodiments, the timing cycle is selectable by a caregiver. The timing cycle may indicate when the catheter tube should be checked, changed, or removed from a patient. The timing cycle may have a default value that may depend upon the type of the catheter and/or the type of the patient with which the catheter is used. The electronic input may comprise an electronic signature of a caregiver, a selection of an icon, or an entry of a code.

In some embodiments, the systems contemplated herein may further include a receptacle that may couple to the catheter tube to receive liquid from the catheter tube and a receptacle RFID tag. The RFID reader may read the receptacle RFID tag such that a time-stamp may be created in response to the receptacle being attached to or detached from the catheter tubing. In some embodiments, the timer accounts for time that the catheter tube was in use with a patient prior to the RFID reader of the patient bed reading the RFID tag. For example, the catheter may have been inserted into a patient during surgery and a time of insertion may be stored in the patient's electronic medical record (EMR) of an EMR system. The timer accounts for the time the catheter was in use prior to the RFID reader reading the RFID tag based on information received from the EMR system.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
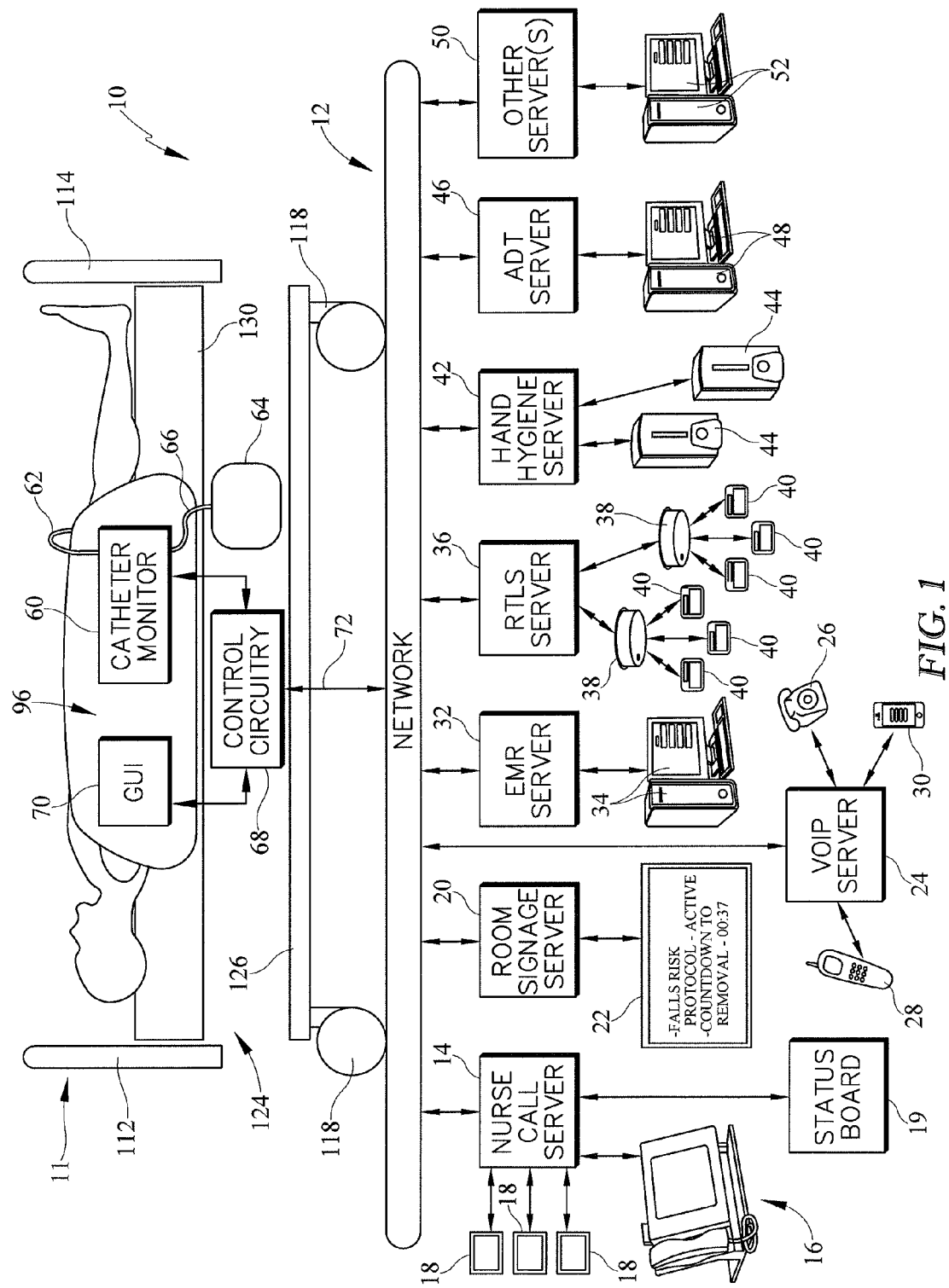
FIG. 1 is a block diagram showing a catheter monitor integrated into a siderail of a patient bed and control circuitry of the patient bed being coupled to a network of a healthcare facility.

According to the present disclosure, a system 10 includes a patient bed 11 that couples to a network 12 of a healthcare facility as shown diagrammatically in FIG. 1. In the illustrative example, network 12 includes a number of other systems each having an associated server. These other systems of network 12 are shown diagrammatically in FIG. 1 and, in the illustrative example, include a nurse call server 14 which is communicatively coupled to a master station 16, a number of graphical room stations 18, and a status board 19 (aka an electronic white board); a room signage server 20 which is communicatively coupled to an electronic room sign 22; a voice over Internet protocol (VOIP) server 24 which is communicatively coupled to one or more standard telephones 26, one or more wireless telephone handsets 28, one or more smart phones 30 and the like; an electronic medical records (EMR) server 32 which is communicatively coupled to one or more EMR computer devices 34; a real time locating system (RTLS) server 36 which is communicatively coupled to a number of RTLS receivers or transceivers 38 which, in turn, communicate with location tags or badges 40 that are worn or carried by caregivers; a hand hygiene server 42 which are communicatively coupled to one or more handwashing agents dispensers 44; and an admission, discharge, and transfer (ADT) server 46 which is coupled to one or more ADT computer devices. One or more other servers 50 and associated computer devices 52 are illustrated generically in FIG. 1 as being part of network 12 of system 10 and are intended to represent all other servers and computer devices included in any given network of a healthcare facility.

It will be appreciated that network 12 of FIG. 1 and the various computer devices 14-52 are a rudimentary depiction of a network of a healthcare facility and that actual networks have many more hardware components than depicted. For additional details of some hardware of a network of a healthcare facility, including details of nurse call systems, room signage systems, hand hygiene systems, and RTLS systems, see the following U.S. Patents and Patent Applications, each of which is hereby expressly incorporated herein by reference to the extent not inconsistent with the present disclosure which shall control as to any inconsistencies: U.S. Pat. Nos. 5,561,412; 5,699,038; 5,838,223; 6,462,656; 6,539,393; 6,727,818; 6,972,683; 7,092,376; 7,242,306; 7,248,933; 7,319,386; 7,734,476; 7,907,053; 8,046,625; 8,169,304; 8,384,526; and 8,598,995; and U.S. Patent Application Publication No. 2014/0244298.

A catheter monitor 60 is coupled to bed 11 as illustrated diagrammatically in FIG. 1. Catheter monitor 60 is coupled to a patient via a first segment of catheter tubing 62 and is coupled to a fluid collection receptacle 64 via a second segment of catheter tubing 66. Thus, urine from the patient flows through tubing 62, 66 and monitor 60 to receptacle 64 for collection. Monitor 60 gathers data regarding the urine flow, volume, etc. and provides that data to control circuitry 68 of bed 11. Control circuitry 68 also receives bed data from various sensors and components of bed 11 as is known in the art. For examples of various types of bed data associated with some embodiments of bed 11, see U.S. Patent Application Publication No. 2012/0316892 which is hereby expressly incorporated by reference herein to the extent not inconsistent with the present disclosure which shall control as to any inconsistencies.

Bed 11 includes a graphical user interface (GUI) 70, such as a touchscreen display, that is electrically coupled to control circuitry 68 of bed 11 and that displays bed data. According to this disclosure, GUI 70 also displays data from catheter monitor 60 in some embodiments. GUI is configured to accept user inputs to control functions of bed 11 and, in some embodiments, to control functions of catheter monitor 60. Control circuitry 68 of bed 11 is configured to send bed data and monitor data to network 12 over a common communication link 72 as shown diagrammatically in FIG. 1. In some embodiments, communication link 72 comprises a wired link such as, for example, a data cable like the 37-pin nurse call cables used in connection with some prior art patient beds available from Hill-Rom Company, Inc. In other embodiments, communication link 72 comprises a wireless link such as those shown and described for example in U.S. Pat. Nos. 7,399,205 and 7,852,208 and in U.S. application Ser. No. 14/487,279, filed Sep. 16, 2014 and titled "Bed/Room/Patient Association Systems and Methods," each of which is hereby expressly incorporated by reference herein to the extent not inconsistent with the present disclosure which shall control as to any inconsistencies.

According to this disclosure, the various devices of network 12 having displays are able to display data from catheter monitor 60 as transmitted to network 12 from bed 11 via link 72. Thus, catheter monitor data is displayed on master station 16, room stations 18, and status board 19 of a nurse call system in some embodiments. Alternatively or additionally, catheter monitor data is displayed on electronic room sign 22 of a room signage system. Further alternatively or additionally, catheter monitor data is displayed on EMR computer device 34 and/or on the display screens of phone 26, handset 28, or phone 30. Tablet computers are an example of another computer device on which catheter monitor data is displayed according to this disclosure. For a discussion of interfacing a tablet computer with a patient bed via a network, see U.S. Patent Application Publication No. 2014/0297327 which is hereby expressly incorporated by reference herein to the extent not inconsistent with the present disclosure which shall control as to any inconsistencies.

Figure 2:
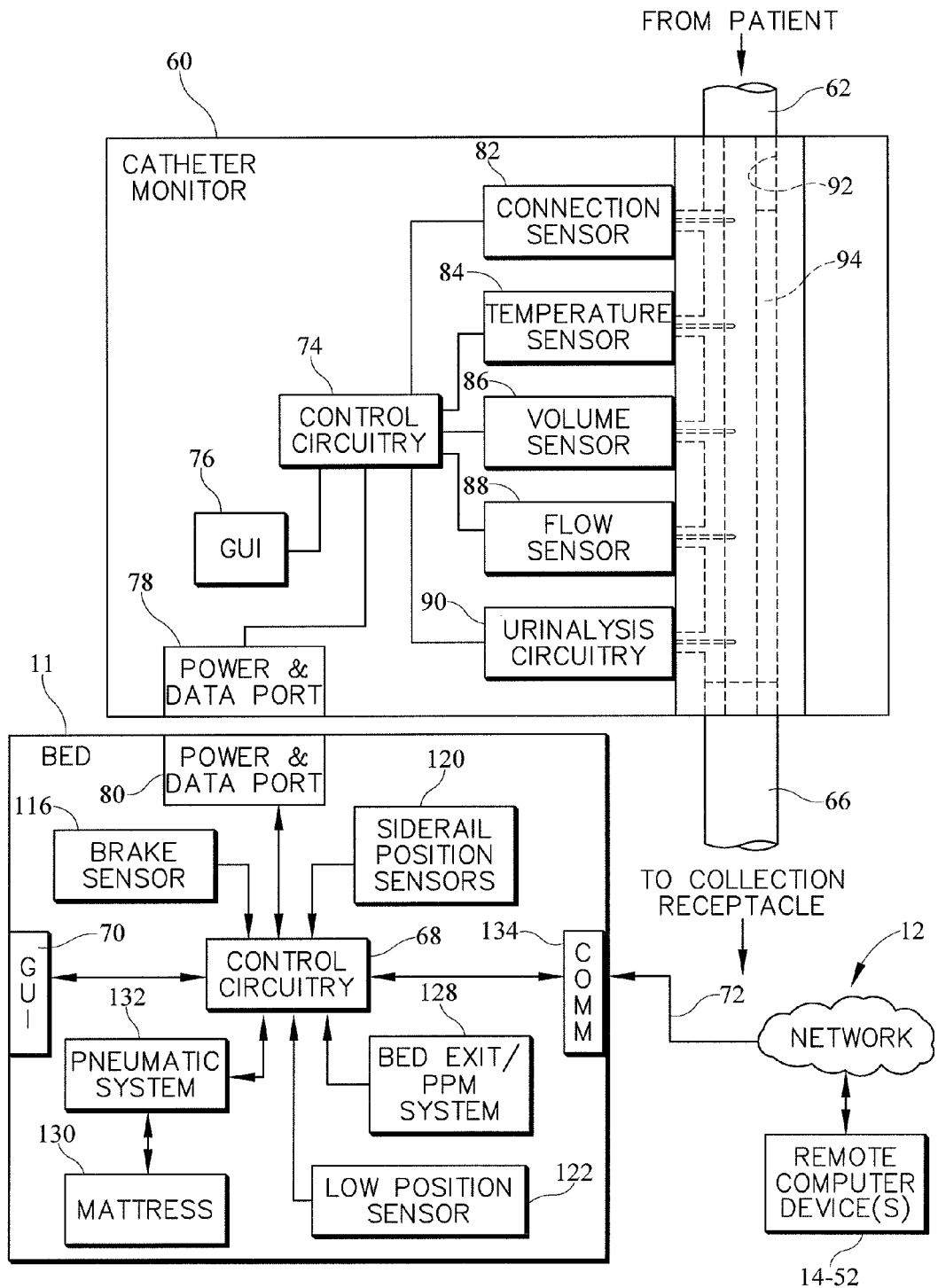
FIG. 2 is a block diagram showing additional details of the catheter monitor circuitry and the bed circuitry and the interconnection between the monitor circuitry and the bed circuitry.

Throughout FIGS. 1 and 2, double headed arrows are used to denote communication links between various components or devices. This is intended to convey the fact that the communication link is a bidirectional communication link in some embodiments. However, that is not to say that, in other embodiments, only a one-way communication is not suitable for any one or more of the illustrative communication links. Accordingly, bidirectional and one-way communication links are contemplated by this disclosure for all communication links. For example, in some embodiments, catheter monitor 60 sends data to circuitry 68 of bed 11, but does not receive any data from circuitry 68 of bed 11. As another example, in some embodiments, tags 40 transmit signals to transceivers 38 but do not receive any signals from transceivers 38.

Referring now to FIG. 2, additional details of catheter monitor 60 and bed 11 are shown diagrammatically. In the illustrative example, catheter monitor 60 includes control circuitry 74, a GUI 76, and a power & data port 78. Port 78 couples to a power & data port 80 of bed 11 when catheter monitor 60 is coupled to bed 11. Port 80 of bed is coupled to circuitry 68 of bed 11. Thus, catheter monitor data from circuitry 74 is communicated to circuitry 68 of bed 11 via ports 78, 80. GUI 76 of catheter monitor 60 displays monitor data and, in some embodiments, also displays bed data. Thus, in such embodiments, GUI 70 of bed 11 can be omitted if desired.

Catheter monitor 60 also includes a connection sensor 82, a temperature sensor 84, a volume sensor 86, a flow sensor 88, and urinalysis circuitry 90. Sensor 82 senses whether tubing 62 is attached to catheter monitor 60 or, more particularly, whether an end of tubing 62 is inserted into a port 92 of a housing of monitor 60. Sensors 84, 86, 88 sense the various aspects of the urine flowing into tubing 62, then through internal tubing 94, and then into tubing 66 that their name implies. Thus, temperature, volume, and flow rate of the urine through monitor 60 is among the data collected by circuitry 74 and transmitted to circuitry 68 of bed 11 and then on to network 12 and the devices associated therewith. In some embodiments, one or more of sensors 82, 84, 86, 88 comprise an optical sensor.

Figure 3:
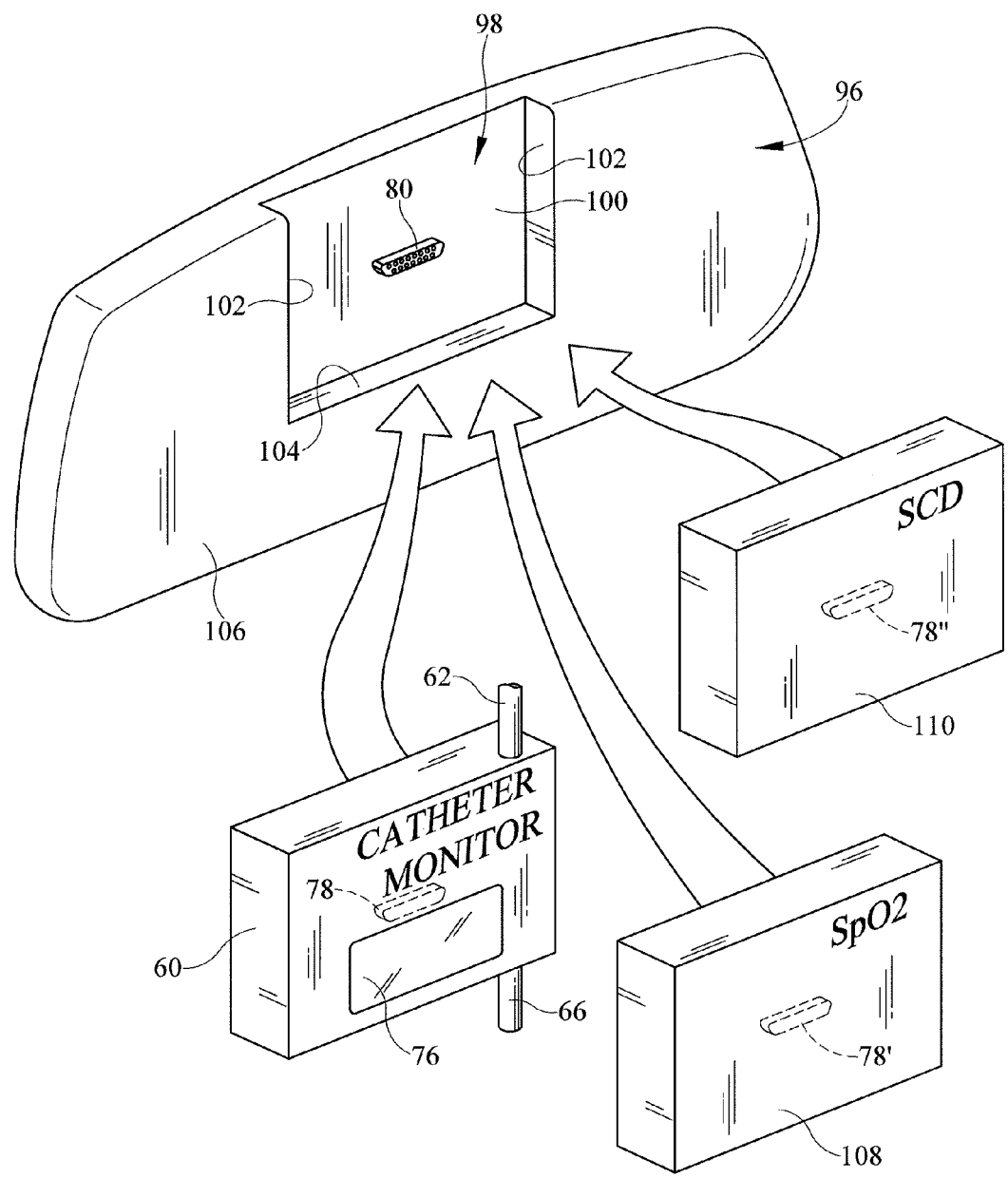
FIG. 3 is a diagrammatic view showing a cavity formed in the siderail of the patient bed being sized to receive the catheter monitor and sized to receive other types of patient care equipment as well.

Referring to FIG. 3, it is contemplated by this disclosure that a siderail 96 of bed 11 has a socket or cavity 98 that is shaped to receive at least a portion of monitor 60 therein. In the illustrative example, port 80 of bed 11 is a male component that projects from a back wall surface 100 of siderail 96 for receipt by a female receptacle of monitor 60 to mate with port 78. Surface 100 cooperates with a pair of side surfaces 102 and a bottom surface 104 of siderail 96 to define cavity 98. However, this is simply one example of a cavity or socket that is suitable for receiving a portion of a catheter monitor according to this disclosure. In the illustrative example, only about half of monitor 60 fits into cavity 98 and the other half of monitor 60 projects beyond a main outer surface 106 of siderail 96. This arrangement permits tubing 66 to extend downwardly from the bottom of monitor 60 without kinking or obstruction from the siderail 96.

It is contemplated by this disclosure that other patient care devices, such as a pulse oximeter 108 or a sequential compression device (SCD) 110, are sized for receipt in cavity 98 of siderail 96 in lieu of catheter monitor 60 as suggested in FIG. 3 by the slightly curved arrows leading from the back of each of these devices and pointing toward cavity 98. Thus, a number of devices are coupleable to bed 11 to provide data to circuitry 68 of bed 11 and then, ultimately, to network 12 via communication link 72. Pulse oximeter 108 has a port 78' and SCD 110 has a port 78" that are configured to mate with port 80 to allow for the data and power transfer.

In some embodiments, bed 11 has cavities 98 provided in its other siderails (e.g., beds typically have four siderails) so that multiple different patient care devices can be coupled to bed 11 at the same time and provide data to circuitry 68 of bed 11 and to receive power from bed 11. Thus, monitor 60 may be attached to one of the siderails of bed 11, pulse oximeter 108 may be attached to another of the siderails of bed 11, SCD 110 may be attached to still another of the siderails of bed 11, and yet another device such as a vital signs monitor (e.g., heart rate monitor, respiration rate monitor, blood pressure monitor, etc.), may be coupled to the remaining siderail of bed 11. It is also within the scope of this disclosure to provide one or more cavities similar to cavity 98 in a headboard 112 and/or a footboard 114 to accommodate coupling of even more patient care devices to bed 11. Siderails, headboards, and footboards are sometimes referred to generically as barriers.

In some embodiments, a latch or other retention mechanism such as one or more snap fingers, ribs, or straps is provided on siderail 96 to help retain catheter monitor 60 and devices 108, 110 in cavity 98. Alternatively, the latch or other retention mechanism is provided on the catheter monitor 60 and devices 108, 110. In some embodiments, cavity 98 is omitted and a bracket, a hook, a strap, a magnet, hook-and-loop patches, or some other coupler is used to couple catheter monitor 60 and devices 108, 110 to siderail 96 or to other portions of bed 11 as desired. It is contemplated by this disclosure that ports 78, 80 are universal serial bus (USB) ports in some embodiments. It is also contemplated that control circuitry 74 of catheter monitor 60 resides on bed 11 in some embodiments. For example, circuitry 68 of bed 11 includes the functionality of circuitry 74 in some embodiments. In some such embodiments, catheter monitor 60 is a disposable cartridge or module that contains one or more of sensors 82, 84, 86, 88 and/or urinalysis circuitry 90, with conductors leading to port 78, but otherwise does not contain additional circuitry. Thus, the processing of the sensor data and urinalysis data is done by circuitry 68 of bed 11.

Referring once again to FIG. 2, bed 11 includes a brake sensor 116 to sense whether casters 118 are braked or released, siderail position sensors 120 to sense whether respective siderails 96 are in raised positions or lowered positions, and a low position sensor 122 to sense whether an upper frame 124 of bed 11 is in a lowered position relative to a base frame 126 of bed 11. Each of sensors 116, 120, 122 is coupled to circuitry 68. Bed 11 also includes a bed exit and/or patient position monitoring (ppm) system 128 coupled to circuitry 68. In some embodiments, bed exit/ppm system 128 of bed 11 includes load cells that are also used to measure a weight of the patient that is present on bed 11. See U.S. Pat. Nos. 6,208,250; 6,438,776; 6,924,441 and 7,253,366 which are hereby incorporated by reference herein to the extent not inconsistent with the present disclosure which shall control as to any inconsistencies for examples of weigh scale systems of patient beds.

Bed 11 also includes a mattress 130 and pneumatic system 132 which is coupled to circuitry 68 as shown diagrammatically in FIG. 2. Pneumatic system 132 includes the various components such as one or more pressure sources (e.g. blower, compressor, or pump), manifolds, valves, pressure sensors, and the like to control the inflation of air bladders or cells of mattress 130. It will be appreciated by those skilled in the art that pneumatic systems and control circuitry of patient beds are complex in nature and that these are shown in the present disclosure in a simplified rudimentary manner. However, additional details of one example of such a pneumatic system and control circuitry for a patient bed can be found in *SERVICE MANUAL, Progressa™ Bed*, From Hill-Rom, © 2013, which is hereby incorporated by reference herein to the extent not inconsistent with the present disclosure which shall control as to any inconsistencies. Finally, bed 11 includes a communication port or module 134 such as a cable connector or a wireless transceiver, for example. Port or module 134 forms a part of the communication link 72 in some embodiments.

According to an aspect of this disclosure, identification data is among the data transmitted from circuitry 68 of bed 11 to network 12. Thus, bed ID data, catheter ID data, other device ID data (e.g., from pulse oximeter 108 and/or SCD 110) and patient ID data is among the data transmitted from bed 11 to network 12. Bed ID data is typically stored in the memory of circuitry 68 of bed 11 although, in some embodiments, bed 11 may have a separate ID tag affixed thereto for transmission of bed ID. Catheter monitor ID is transmitted from monitor 60 to bed 11 along with its other data. As to patient data, in some embodiments, bed 11 includes a reader, such an RFID reader to read a signal transmitted from an RFID tag (e.g., included in a wristband) worn by the patient. One or more of the patents and patent applications already incorporated by reference herein include disclosures concerning beds that receive patient ID data. See also U.S. Provisional Patent Application No. 62/073,098, filed Oct. 31, 2014 and titled "Equipment, Dressing and Garment Wireless Connectivity to a Patient Bed," which is hereby expressly incorporated by reference herein to the extent not inconsistent with the present disclosure which shall control as to any inconsistencies. Thus, by having the ID data of the patient and the various associated devices, including catheter monitor 60, nurse call server 14, room signage server, and EMR server 32 are able to store and display for each patient, the associated bed data, device data, and catheter monitor data.

Other types of data included among the bed data and catheter monitor data include alarm data and diagnostic data. For example, if one of tubes 62 or 66 become disconnected from catheter monitor 60 a tube disconnection alarm is generated by circuitry 74 in some embodiments. Other circuitry faults such a watchdog timer timing out or a short circuit being detected or other circuitry damage being detected are also examples of type of alarms that may be generated by circuitry 68 or circuitry 74 as appropriate.

According to another aspect of the present disclosure, a falls prevention protocol is implemented by circuitry 68 of bed 12 automatically based on data received from catheter monitor 60. For example, control circuitry 68 may implement the falls prevention protocol in response to a signal from the catheter monitor 60 indicating at least one of the following: the catheter monitor 60 being turned on, a catheter tube 62 or 66 being attached to the catheter monitor, and urine flowing through the catheter monitor 60. It will be appreciated that a catheterized patient is considered a falls risk patient and that they should not exit bed 11 while catheterized.

The falls prevention protocol (aka falls risk protocol) includes an alert being generated by bed 12, or in some embodiments, by server 14, to indicate one or more of the following conditions of bed 11: casters 118 of bed 11 are not braked; at least one siderail 96 of bed 11 is not in a raised position; upper frame 124 of bed 11 is not in a lowered position relative to base frame 126 of the patient support apparatus. The associated sensors 116, 120, 122 provide the signals to circuitry 68 that permit these determinations to be made. The falls prevention protocol also includes an alert being generated if bed exit/ppm system 128 of bed 11 indicates that the patient has exited bed 11 or has moved toward exiting bed 11 by a threshold amount.

In some embodiments, control circuitry 68 sends a nurse call signal to server 14 or master station 16 in response to a violation of the falls risk protocol. In some embodiments, control circuitry 68 sends data to EMR server 32 pertaining to operation of the catheter monitor or implementation of the falls risk protocol or both. Furthermore, control circuitry 68 sends data to server 20 which signals electronic room sign 22 to display information that may pertain to the falls risk protocol. In the illustrative example, electronic room sign 22 includes the text "FALLS RISK PROTOCOL—ACTIVE."

According to a further aspect of the present disclosure, either control circuitry 68 of bed 11 or control circuitry 74 of monitor 60 or both is operable to implement a countdown timer to indicate an amount of time before catheter tubing 62 should be removed from the patient (referred to herein as "countdown to removal"). In some embodiments, the countdown timer is activated in response to a signal from catheter monitor 60 indicating at least one of the following: the catheter monitor 60 being turned on, a catheter tube 62 or 66 being attached to the catheter monitor, and urine flowing through the catheter monitor 60.

In some embodiments, an initial period of time at which the countdown timer is set may be no longer than 24 hours. It is contemplated by this disclosure that an alert may be initiated by control circuitry 68 or monitor circuitry 74 in response to expiration of the countdown timer. Alternatively or additionally, an alert may be initiated by control circuitry 68 or circuitry 74 a preset amount of time prior to the expiration of the countdown timer. It is contemplated by this disclosure that the countdown timer may be displayed on one or more of GUI 70, GUI 76, room stations 18, master station 16, status board 19, electronic room sign 22, phones 26, 28, 30, and/or computer devices 34, 48, 52 via the associated servers 14, 20, 24, etc. In the illustrative example, electronic room sign 22 includes the text "COUNTDOWN TO REMOVAL—00:37." In some embodiments, circuitry 68 or circuitry 74 sends a nurse call signal to nurse call server 14 or master station 16 in response to expiration of the countdown timer or upon a preset amount of time prior to the expiration of the countdown timer being reached.

As alluded to above, catheter monitor 60 includes a housing and tubing 62, 66 couples to this housing. In some embodiments, a module carries some of the monitor circuitry and tubing 62, 66 couples to the module. For example, such a module includes internal tubing 94, sensors 82, 84, 86, 88, and urinalysis circuitry 90 in some embodiments. The module detachably couples to the housing such that the module with its associated monitor circuitry and the tubing 62, 66 are disposable after use. The collection receptacle 64 is also disposable after use. Thus, circuitry 74 of catheter monitor 60 serves as interface circuitry that is carried by the housing on a permanent basis. The interface circuitry 74 then interconnects the monitor circuitry with the bed circuitry 68 when the module is coupled to the housing of the catheter monitor 60. In some embodiments, bed 11 includes a user input either on the GUI 70 or separate from the GUI 70 that may be selected by a caregiver to confirm the accuracy of at least some of the monitor data. By selecting this particular user input, monitor data is sent to EMR server 32, for example, with a "confirmed reading" message being included for storage along with the data.

According to yet another aspect of the present disclosure, one or more of servers 14, 32, 42, 50 checks to determine if a caregiver has washed their hands within a threshold amount of time of connecting catheter tubing 62 to the patient. Under such circumstances, the server doing the checking is considered to be a "compliance monitoring computer" according to this disclosure. For example, when sensor 82 of catheter monitor 60 senses connection of catheter tubing 62 to port 92, it is assumed that the tubing 62 was connected or will be connected to the patient a very short time period thereafter or therebefore. The compliance monitoring computer communicates with server 42, or if server 42 is the compliance monitoring computer, checks its own databases, to determine when the caregiver last washed his or her hands using one of dispensers 44. In this regard, the identity of the caregiver is determined based on the tag 40 worn by the caregiver being sensed by transceiver 38 in the same room as catheter monitor 60.

The compliance monitoring computer determines whether the caregiver attaching the catheter tubing 62 to the catheter monitor 60 used the hand hygiene system dispenser 44 for handwashing less than a threshold amount of time prior to connecting the catheter tubing 62 to the catheter monitor 60. In some embodiments, the threshold amount of time for handwashing may be selectable using the compliance monitoring computer. An alert is generated by the compliance monitoring computer if the catheter tubing 62 is connected to the catheter monitor 60 and the caregiver did not use one of the hand hygiene system dispensers 44 within the threshold amount of time prior to connecting the catheter tubing 62 to the catheter monitor 60. The alert may include a message displayed one or more of the following: GUI 70, GUI 74, one or more room stations 18, master station 16, status board 19, electronic room sign 22, a display of one of phones 26, 28, 30, and a tablet computer display.

By monitoring for compliance with handwashing protocols in connection with use of catheter monitor 60, it is contemplated that the number of incidents of catheter-associated urinary tract infection (CAUTI) will be decreased in a healthcare environment. Typically, a catheter is removed at least 24 hours after insertion. In some instances, however, caregivers may affirmatively decide to continue the use of the catheter. According to some embodiments, therefore, a user input is provided on bed 11 or catheter monitor 60 for selection by a caregiver to affirmatively indicate that the catheter should continue to be used after the countdown to removal time period expires. Selection of the user input resets the countdown timer either to the initial countdown period or to some other programmed time period that is either preprogrammed to a default period or selected by a user. The user input comprises a button or icon on GUI 70 or GUI 76 in some embodiments. Fields for setting the countdown time period and reset time period also are provided on GUI 70 or GUI 76 in some embodiments.

Bed 11 or catheter monitor 60 of system 10, therefore, uses a recognizable event such as connection of tubing 62 to catheter monitor 60 for triggering a CAUTI protocol including initiating a 24 hour countdown timer, communicating status relative to the countdown, and creating notifications that the protocol has not been followed (e.g., tubing 62 has not been removed from the patient in a timely manner or re-authorized for continued use). In some embodiments, EMR server 32 or some other server documents (e.g., collects and stores) the information relating to compliance with the CAUTI protocol.

As mentioned above, tubing 62, 66 and, in some embodiments, an additional module, is included as part of a catheter kit. It is contemplated by this disclosure that, in some embodiments, the catheter kit has a transmitter that transmits a wireless kit-opened signal indicating that the kit is being opened or has been opened. A receiver of network 12, such as one of receivers 38, receives the kit-opened signal and forwards it on to the compliance monitoring computer. The compliance monitoring computer, after receiving the kit-opened signal, determines whether the caregiver opening the catheter kit has used one of the hand hygiene system dispensers 44 for handwashing within a threshold amount of time prior to or after receipt of the kit-opened signal. The RTLS system 36, 38, 40 is used for determining the caregiver who has opened the kit.

According to this disclosure, one or more of the various displays 16, 18, 19, 22, 70, 74 of system 10 display activities required by a healthcare protocol. The healthcare protocol may comprise, for example, activities that include one or more of: wearing a gown, wearing sterile gloves, wearing a mask, draping a patient with a sterile sheet, and use of an antiseptic such as chlorhexidine. Alternatively or additionally the display may be included as part of one or more of phones 26, 28, 30 and/or a tablet computer display. In some embodiments, system 10 includes RF transmitters that are affixed to one or more of the gown, the gloves, the mask, and the drape. System 10 further includes RF receivers that receive signals from the RF transmitters to determine compliance with the healthcare protocol.

The compliance monitoring computer receives caregiver identification (ID) data from the locating system 36, 38, 40 and determines whether the caregiver identified by the caregiver ID data has received proper training to implement the healthcare protocol. In some embodiments, the compliance monitoring computer determines that a patient's condition meets established criteria for the healthcare protocol based on patient data received by the compliance monitoring computer.

Alternatively or additionally, the compliance monitoring computer may receive caregiver identification (ID) data and caregiver location data from the locating system 36, 38, 40 and may confirm that the caregiver has not been exposed to infectious agents within a threshold amount of time prior to opening the catheter monitoring kit. An alert is generated by the compliance monitoring computer if the caregiver has been exposed to infectious agents within the threshold amount of time. The alert includes a message displayed on at least one of the following: GUI 70, GUI 74, master station 16, one or more of room stations 18, a status board 19, an electronic room sign 22, a phone display of one or more of phones 26, 28, 30, a tablet computer display, or a display of one or more of computer devices 34, 48, 52.

Based on the foregoing, it should be appreciated that, in some embodiments, catheter monitor 60 contains all components necessary to perform urine assessment (e.g., optical sensor and processor to compute volume and flow of urine); to collect, store, and display data; and also includes the user controls (e.g., GUI 76) for providing inputs to circuitry 74. The urine from the patient flows through catheter monitor 60 and into collection receptacle 64 via tubing 62, 66. In some embodiments, catheter tubing 62 includes a temperature sensor in the portion that is inserted into the patient and is used to measure the patient's core temperature. In some such embodiments, an electrical conductor is embedded in tubing 62. Bed 11 provides a physical mounting location for monitor 60 and provides power and data connectivity for monitor 60.

In some embodiments, attachment of the sensor module or cartridge discussed above to the rest of catheter monitor 60 is used as the trigger to assess handwashing compliance monitoring, to begin the countdown to removal timer or to initiate the falls prevention protocol. A switch is used to sense the attachment of the cartridge or tubing 62, 66 in some embodiments. Thus, catheter monitor 60 senses an event, such as connection of tubing or connection of sensor cartridge, and automatically communicates data about the occurrence of the event to bed 11 for ultimate communication to network 12. In some embodiments, bed 11 sends patient ID with catheter start time and one or more of servers 14, 20, 32, 50 implement the countdown to removal protocol and communicate countdown timer information to bed 11 for display on GUI 70, to one or more of wireless communication devices 38, 30 for display, to status board 19 for display, or to other devices for display, such as devices 16, 18, 34, 48, 52. Alternatively or additionally, the event sensed by catheter monitor triggers an infection prevention protocol and information about the protocol is displayed on the various devices of system 10.

By integrating catheter monitor 60 with bed 11, circuitry 74 of monitor 60 has access to data stored in circuitry 68 of bed 11, such as location ID data, patient ID data, vital signs data, bed status data, patient weight and other data pertaining to characteristics of the care environment. Furthermore, monitor 60 has access to the communication capabilities of bed 11 such as RF, other wireless (e.g., IR or ultrasound or wideband), barcode scanning, near field communication technology, etc., to the extent that bed 11 is equipped with such technologies.

Figure 4:
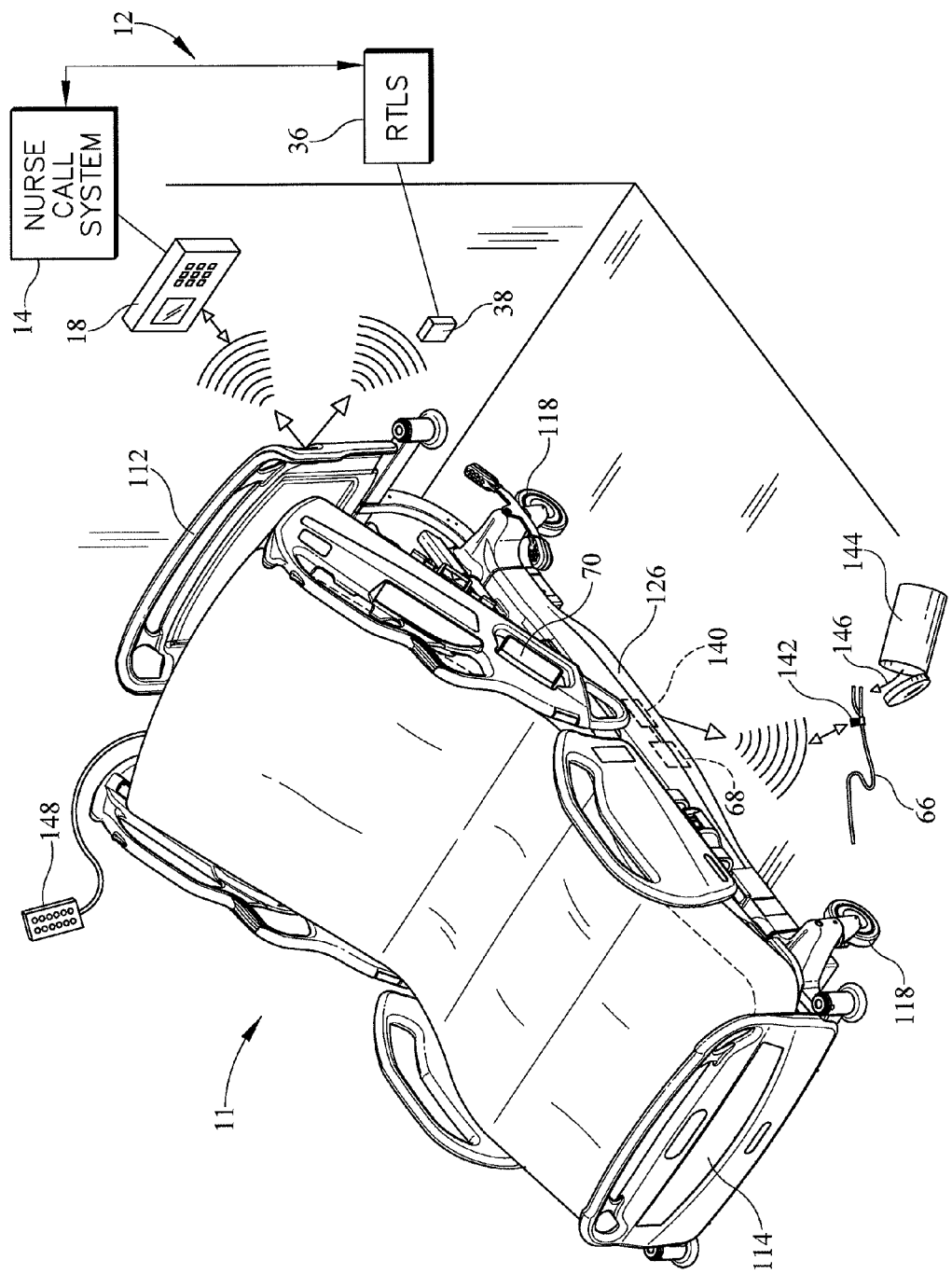
FIG. 4 is a perspective view showing a patient bed having a radio frequency identification (RFID) reader to read an RFID tag attached to catheter tubing that has been removed from metallic foil packaging that blocks the ability of readers to read the tag until removal.

Referring now to FIG. 4, bed 11 includes a radio frequency identification (RFID) reader 140 coupled to circuitry 68 (shown diagrammatically in FIG. 4 in phantom). RFID reader 140 reads an RFID tag 142 that is attached to catheter tubing 66. Prior to use, the catheter tubing 66 having RFID tag 142 is removed from metallic foil packaging 144 as indicated by arrow 146 in FIG. 4. Prior to removal, the metallic foil packaging 144 blocks RFID tag 142 from being read by RFID reader 140, or really, any RFID reader for that matter. By having RFID reader 140 integrated into bed 11, a separate hand held RFID scanner does not need to be used to read tag 142. Furthermore, a catheter monitor 60 of the type discussed above does not need to be used in connection with the FIG. 4 embodiment.

In some embodiments contemplated by this disclosure, RFID reader 140 reads other RFID tags that are in proximity to bed 11 as well as reading tag 142. For example, RFID reader 140 is able to read RFID tags included in patient wrist bands; garments such as compression sleeves, sequential compression sleeves, vests or wraps of high frequency chest wall oscillation systems, red socks to indicate that a patient is a falls risk, and patient gowns; wound dressings; and other equipment used for patient care such as intravenous (IV) pumps, sequential therapy pumps, therapy devices such as passive motion machines, physiological monitoring devices, ventilation equipment, and the like. In this regard, see U.S. Provisional Patent Application No. 62/073,098, filed Oct. 31, 2014, and titled "EQUIPMENT, DRESSING AND GARMENT WIRELESS CONNECTIVITY TO A PATIENT BED."

Still referring to FIG. 4, the ID information read by reader 140 from tag 142, as well as any other ID information read by reader 140, is transmitted from bed 11 to RTLS server 36 via receiver 38 and/or is transmitted from bed 11 to nurse call system server 14 via room station 18. Such transmissions from bed 11 to receiver 38 and/or room station 18 are made via communication port 134 (see FIG. 2) in some embodiments. In some embodiments, a separate tag 40 on bed 11 sends its ID to receiver 38 which, in turn, sends the tag ID and a receiver ID to RTLS server 36. The RTLS server 36 and/or nurse call server 18 associates the catheter tubing ID from tag 142 with one or more of the ID's of bed 11 (or tag 40 coupled thereto), the patient, the room in which bed 11 is located, and the caregiver assigned to the patient.

The catheter tubing ID and one or more of the other ID's are also stored in the patient's electronic medical record of EMR server 32 in some embodiments. In some embodiments, bed 11 receives a room ID from communication device 38 which serves as a transmitter 38 or transceiver 38 in such embodiments and then bed 11 re-transmits the room ID along with other bed data and ID's, including the catheter tubing ID, from the associated communication port 134 (see FIG. 2) of bed 11 to room station 18 and hence to Nurse Call System 14. Nurse Call System 14, in turn, provides the ID data to RTLS server 36 in some embodiments.

In response to reader 140 receiving the transmission from tag 142 of catheter tubing 66, a timer is started automatically to monitor how long the catheter has been in use. Alternatively, in response to reader 140 receiving the transmission from tag 142 of catheter tubing 66, a caregiver is prompted on a display, such as GUI 70 of bed and/or the display of room station 18 and/or the display of a handheld pendant controller 148 of bed 11, to enter an electronic signature or other type of user input (e.g., selection of a particular icon or button, entry of a code, etc.) and then the timer is started in response to receipt of the electronic signature of the caregiver or the other type of user input serving as the prompt on GUI 70. If desired, the caregiver waits until the catheter is inserted into the patient to enter the electronic signature or other prompted input to thereby start the timer. Such a timer is included in room station 18 in some embodiments, is included as part of control circuitry 68 in some embodiments, and/or is included in circuitry of handheld pendant controller 148 in some embodiments. Regardless of its location, the timer is a countdown timer in some embodiments that counts down by a predetermined amount, such as 24 hours. The countdown time amount may be considered a timing cycle according to this disclosure. Thus, removal of tubing 66 having tag 142 from packaging 144 and reading tag 142 by reader 140 is another event that begins a timer according to this disclosure. In some embodiments, the reading of tag 142 by reader 144 is also a triggering event for monitoring handwashing compliance as described above.

The discussion above regarding the use of a timer and a countdown-to-removal protocol of the catheter 66 is equally applicable to the embodiment depicted in FIG. 4. Accordingly, a countdown time is displayed on GUI 70 of bed 11 and/or on a display screen of pendant 148 and/or on a display of room station 18 in some embodiments. An alert message is also displayed on one or more of these devices 18, 70, 148 at the end of the countdown time in some embodiments and/or at a predetermined time prior to the end of the countdown time. Alternatively or additionally, an alert message regarding the end of the countdown time being reached or regarding the end of the countdown time being reached in the near future is communicated to one or more caregivers, such as being communicated to a wireless communication device carried by the caregiver(s), in some embodiments. Bed 11 and/or room station 18 automatically initiates a nurse call to nurse call server 14 at the end of the countdown timer or a predetermined amount of time prior to the end of the countdown timer in some embodiments.

In some embodiments, a caregiver enters on GUI 70, room station 18, or pendant controller 148, a countdown time of their choosing which may be greater than or less than the 24 hour default countdown time. Alternatively or additionally, the caregiver is able to use one or more of devices 18, 70, 148 to enter other times at which the catheter is to be checked prior to countdown-to-removal time expiration (e.g., checking every 6 hours or every 8 hours, just to name a couple possible examples). Thus, the caregiver is able to enter pre-determined time limits and to be notified by the system of FIG. 4 as to when the catheter should be checked, changed or removed. The notification is made via the nurse call system 14 in some embodiments.

The times entered by the caregiver for catheter removal, or automatically determined by one or more of the computer devices 14, 18, 68, 148 of the system of FIG. 4 or some other computer device of network 12, is based on the type of catheter being used, the type of patient with which the catheter is being used, or both. For example, indwelling catheters may need to be changed more frequently than external (e.g., condom) catheters or less frequently than short term or intermittent catheters. Catheters may need to be changed more frequently for children than for adults or more frequently when the patient has undergone bladder surgery rather than knee surgery, just to name a couple of examples. The type of catheter is able to be determined based on the catheter ID read by reader 140 from tag 142 and the type of patient is able to be determined based on patient ID read by reader 140 or otherwise stored in RTLS server and/or nurse call server 14 and/or some other server of the associated system.

In some embodiments, the systems contemplated herein include a receptacle that couples to the catheter tube 66 to receive liquid (e.g., urine) from the catheter tube. The receptacle has its own receptacle RFID tag in some embodiments. The RFID reader 140 reads the receptacle RFID tag such that a time-stamp is created in response to the receptacle being attached to or detached from the catheter tube 66. Thus, the receptacle is contained within metallic foil packaging similar to packaging 144 so that its receptacle RFID tag is not read until the receptacle has been removed from its packaging. The reading of the receptacle ID by reader 140 is considered a triggering event for handwashing compliance according to some embodiments of this disclosure, the assumption being that the caregiver attaching a new receptacle is doing so in connection with removing an older receptacle containing liquid. Such a receptacle replacement operation is sometimes a source of contamination or potential infection due to accidental spillage.

In some embodiments, the timer in the systems disclosed herein account for time that the catheter tube 66 was in use with a patient prior to the RFID reader 140 of the patient bed 11 reading the RFID tag 142. For example, the catheter tube 66 may have been inserted into a patient during surgery and a time of insertion may be stored in the patient's electronic medical record (EMR) of the EMR system or server 32. The timer accounts for the time the catheter tube 66 was in use prior to the RFID reader 140 reading the RFID tag 142 based on information received from the EMR system 32 or from some other computer device coupled to network 12. Accordingly, the countdown time is reduced by the amount of time the catheter tube 66 was in previous use.

The description above regarding protocol compliance associated with use of catheter monitor 60 (e.g., handwashing protocol compliance, infection protocol compliance, countdown to removal protocol, etc.) or the protocol compliance associated with the use of catheter 66 having tag 142 is applicable to other medical devices, equipment, and kits as well. Generally speaking, this disclosure contemplates that system 10 of FIGS. 1-4 automatically begins monitoring for protocol compliance upon a physical activity associated with the process governed by that protocol.

Many medical procedures create risks (e.g., infection, incompatibility, improper use), and care institutions have implemented protocols reflecting best practices in performing the procedure. Unfortunately, caregivers may not comply with these protocols in any specific instance, for a number of reasons (including ignorance of the protocol, inadequate training, and perceived lack of value in protocol). Institutions may seek to monitor for compliance with these protocols, either to alert of an unsafe condition, to track overall compliance rates, or to perform root cause analysis.

A key challenge in monitoring for protocol compliance is recognizing that the activity governed by that protocol is taking place. According to this disclosure, it is recognized that there is often a physical act that is part of the activity governed by the protocol. For example, for the protocol associated with placing a central line (e.g., an intravenous line such as a peripherally inserted central catheter (PICC) line), the first (or at least significant) physical act is opening the central line kit. Opening the kit triggers a signal from a transmitter of the kit to a receiver of system 10 which results in monitoring for protocol compliance by one or more of servers 14, 20, 32, 42, 50 or the related devices 16, 18, 19, 22, 34, 52. In the description that follows, these are simply referred to as system 10.

Once the system 10 recognizes that an activity governed by a protocol is taking pace, the system 10 begins to monitor for the specific activities and conditions that are required by the protocol for inserting a central line are followed (both prior to and after that act of opening the central line kit). For example, there are specific protocols associated with the insertion of a central line (Central Line Bundle)—one sample protocols includes (1) compliance with hand hygiene protocols, including both physical hand washing and use of disinfectants, (2) use of full-coverage barriers (including wearing sterile gloves, gown, and mask, and draping patient with sterile sheet, (3) use of chlorhexidine as an antiseptic. A more exhaustive summary of central line protocols can be found at jointcommission.org/assets/1/18/CLABSI_Monograph.pdf.

The system 10 communicates the protocol activities to the caregiver at the point of care (e.g., nurse call, text message, display on nurse call or other GUI, or display in dynamic room signage). In some embodiments, the system 10 uses a variety of sensing methods (e.g., passive RF, active RF, access controls, hand hygiene compliance monitoring, RTLS, visual monitoring) to determine whether the protocols are being followed (e.g., to detect that chlorhexidine is present in the room, that a sterile draping has been taken from the supply unit).

Examples of protocols monitored by system 10 according to this disclosure include the following: insertion of a PICC line (protocol compliance monitoring initiated on opening PICC line kit); insertion of Foley catheter (protocol compliance monitoring initiated on opening Foley catheter kit); use of a ventilator (Ventilator Associated Pneumonia ("VAP") bundle triggered by presence of ventilator in room and/or opening disposable vent tube); and protocols related to the performance of a medical procedure, where a physical component is necessary to the performance of that procedure.

Addition of a communications mechanism (e.g., transmitter) to a physical component, in which communication to the system 10 is initiated by use of the component is contemplated by this disclosure. In some embodiments, the component has one or more of the following characteristics: it is a single-use device or consumable, it is only used in performance of the activity governed by the protocol, and it is used early enough in the activity governed by the protocol for monitoring to take place prior to the creation of an unsafe condition.

In addition to receiving transmissions from a component triggered by its use (e.g., opening of a kit), system 10 monitors for performance of activities or existence of conditions required by the protocol for that procedure such as for example: sensing of caregiver identity and reference to system describing caregiver characteristics, to confirm that the caregiver has the required training (e.g., caregiver is RN, caregiver has received infection control training) and has not been exposed to situations incompatible with that procedure (e.g., presence in ward where MRSA is being treated within past 72 hours); sensing of presence of required materials (e.g., RF antenna recognizes that sterile gown and antiseptics are present); and sensing of patient condition (e.g., vitals monitoring confirms that blood pressure is within range for procedure to be performed). Thus, enhanced patient safety through avoidance of errors caused by failure to comply with one or more protocols is the aim of system 10 according to some embodiments contemplated herein.

Although certain illustrative embodiments have been described in detail above, variations and modifications exist within the scope and spirit of this disclosure as described and as defined in the following claims.

The invention claimed is:

1. A patient bed comprising
a frame configured to support a patient,
a barrier coupled to the frame and configured to inhibit patient egress from the frame,
a catheter monitor, the barrier having a cavity shaped to receive at least a portion of the catheter monitor, and
bed control circuitry carried by the frame and configured to control at least one function of the patient bed, the catheter monitor having monitor circuitry in communication with the bed control circuitry.

2. The patient bed of claim 1, further comprising at least one graphical user interface (GUI) coupled to the bed control circuitry, the GUI being operable to display bed information pertaining to the at least one function of the patient bed and to display monitor information pertaining to at least one function of the catheter monitor.

3. The patient bed of claim 1, wherein the bed control circuitry is configured to communicate to a network of a healthcare facility bed information pertaining to the at least one function of the patient bed and monitor information pertaining to at least one function of the catheter monitor.

4. The patient bed of claim 1, wherein the bed control circuitry is configured to communicate to a network of a healthcare facility bed identification (ID) data and catheter monitor identification (ID) data.

5. The patient bed of claim 4, wherein the bed control circuitry is configured to communicate to the network of the healthcare facility patient identification (ID) data.

6. The patient bed of claim 1, further comprising an additional piece of patient care equipment, the cavity being sized to receive at least a portion of the additional piece of patient care equipment when the catheter monitor is removed from the cavity.

7. The patient bed of claim 6, wherein the additional piece of patient care equipment comprises a pulse oximeter or a sequential compression device.

8. A patient support apparatus comprising
a patient support structure to support a patient,
control circuitry to control at least one function of the patient support structure, the control circuitry being operable to implement a falls prevention protocol, and
a catheter monitor coupled to the patient support structure, the control circuitry implementing the falls prevention protocol in response to a signal from the catheter monitor indicating at least one of the following: the catheter monitor being turned on, a catheter tube being attached to the catheter monitor, and urine flowing through the catheter monitor.

9. The patient support apparatus of claim 8, wherein the falls prevention protocol comprises an alert being generated to indicate at least one or more of the following: that casters of the patient support apparatus are not braked or that at least one siderail of the patient support apparatus is not in a raised position or that an upper frame of the patient support apparatus is not in a lowered position relative to a base frame of the patient support apparatus.

10. The patient support apparatus of claim 8, wherein the falls prevention protocol comprises an alert being generated if a patient position monitoring system of the patient support apparatus indicates that the patient has exited the patient support apparatus or has moved toward exiting the patient support apparatus by a threshold amount.

11. The patient support apparatus of claim 8, wherein the control circuitry sends a nurse call signal to at least one remote nurse call system computer device in response to a violation of the falls risk protocol.

12. The patient support apparatus of claim 8, wherein the control circuitry sends data to at least one remote computer device of an electronic medical records system pertaining to operation of the catheter monitor or implementation of the falls risk protocol or both.

13. The patient support apparatus of claim 8, wherein the control circuitry sends data to at least one computer device that signals an electronic room sign to display information pertaining to the falls risk protocol.

14. A system comprising
a patient bed,
a catheter monitor mounted to the patient bed, the catheter monitor having a sensor to sense connection of catheter tubing thereto,
a hand hygiene system that a caregiver uses for handwashing and that monitors for handwashing compliance by caregivers, and
a compliance monitoring computer that, in response to a catheter tubing being connected to the catheter monitor, determines whether the caregiver attaching the catheter tubing to the catheter monitor used the hand hygiene system for handwashing less than a threshold amount of time prior to connecting the catheter tubing to the catheter monitor.

15. The system of claim 14, further comprising a locating system to determine the location of the caregiver in a healthcare facility, the locating system being in communication with the hand hygiene system and with the compliance monitoring computer.

16. The system of claim 14, wherein the threshold amount of time is selectable using the compliance monitoring computer.

17. The system of claim 14, wherein an alert is generated by the compliance monitoring computer if the catheter tubing is connected to the catheter monitor and the caregiver did not use the hand hygiene system within the threshold amount of time prior to connecting the catheter tubing to the catheter monitor.

18. The system of claim 17, wherein the alert comprises a message displayed on at least one of the following: a graphical user interface (GUI) of the patient bed, a GUI of the catheter monitor, a room station of a nurse call system, an electronic room sign, a phone display, and a tablet computer display.

19. A system comprising
a catheter kit including catheter tubing, the catheter kit including a transmitter to transmit a kit-opened signal indicating that the kit is being opened or has been opened,
a hand hygiene system that a caregiver uses for handwashing and that monitors for handwashing compliance by caregivers, and
a compliance monitoring computer that receives the kit-opened signal and determines whether the caregiver opening the catheter kit has used the hand hygiene system for handwashing within a threshold amount of time prior to or after receipt of the kit-opened signal.

20. A system comprising
a patient bed having an RFID reader,
a catheter tube,
an RFID tag attached to the catheter tube, and
a timer that begins a timing cycle in response to the RFID reader reading the RFID tag attached to the catheter tube, and
metallic foil packaging in which the catheter tube and the RFID tag are contained prior to use, the metallic foil packaging preventing the RFID reader from reading the RFID tag until after the catheter tube with the RFID tag attached thereto is removed from the metallic foil packaging.

21. A system comprising
a patient bed having an RFID reader,
a catheter tube,
an RFID tag attached to the catheter tube, and
a timer that begins a timing cycle in response to the RFID reader reading the RFID tag attached to the catheter tube, wherein the timing cycle comprises a countdown time and expiration of the countdown time indicates a time at which the catheter tube is to be removed from the patient.

22. The system of claim 21, wherein an initial period of time at which the countdown time is set is no longer than 24 hours.

23. The system of claim 21, wherein an alert is initiated in response to expiration of the countdown time or is initiated a preset amount of time prior to the expiration of the countdown time.

24. The system of claim 21, wherein the patient bed includes a graphical user interface (GUI) and wherein the countdown time is displayed on the GUI.

25. The system of claim 21, wherein the patient bed sends data to at least one remote computer device of an electronic medical records system pertaining to the countdown time.

26. The system of claim 21, wherein the patient bed sends data to at least one computer device that signals an electronic room sign to display information pertaining to the countdown time.

27. A system comprising
a patient bed having an RFID reader,
a catheter tube,
an RFID tag attached to the catheter tube,
a graphical user interface (GUI), wherein in response to the RFID reader reading the RFID tag attached to the catheter tube, a prompt is displayed on the GUI for an electronic input to be entered by a caregiver, and
a timer that begins a timing cycle in response to entry of the electronic input by the caregiver on the GUI.

28. The system of claim 27, further comprising metallic foil packaging in which the catheter tube and the RFID tag are contained prior to use, the metallic foil packaging preventing the RFID reader from reading the RFID tag until after the catheter tube with the RFID tag attached thereto are removed from the metallic foil packaging.

29. The system of claim 27, wherein the GUI is integrated into the patient bed or is included as part of a room station of a nurse call system or is included as part of a handheld controller.

30. The system of claim 27, wherein the electronic input comprises an electronic signature of a caregiver, a selection of an icon, or an entry of a code.

* * * * *